United States Patent [19]

Mojonnier

[11] Patent Number: Plant 7,692

[45] Date of Patent: Oct. 29, 1991

[54] ALSTROEMERIA PLANT NAMED LILIANA

[76] Inventor: Erwin Mojonnier, 237 Quail Dr., Encinitas, Calif. 92024

[21] Appl. No.: 556,432

[22] Filed: Jul. 24, 1990

[51] Int. Cl.[5] ..... A01H 5/00

[52] U.S. Cl. ..... Plt./68

[58] Field of Search ..... Plt./68, 87.1

*Primary Examiner*—Howard J. Locker

*Attorney, Agent, or Firm*—Foley & Lardner

[57] ABSTRACT

An Alstroemeria plant named Liliana, characterized by its flowers which have a relatively bright red-purple background color, and upper petals which are heavily streaked by grayed-purple, and which have regions of yellow patches and infused white; few non-flowering stems; winter production beginning in mid-November, and good post-harvest color retention.

1 Drawing Sheet

The present invention relates to a new and distinct cultivar of Alstroemeria plant hereinafter referred to by the cultivar name Liliana.

Liliana is a product of a planned breeding program which had the primary objectives of creating new Alstroemeria cultivars having unique flower color and being capable of early winter production with low maintenance requirements. The latter term refers to the production of a minimum of non-flowering stems. Such traits in combination were not present in previously available commercial cultivars.

In order to fully understand an important characteristic of the new cultivar, an explanation of typical current winter production schedules for cut flowers of Alstroemerias would be helpful. Standard industry growing practices normally utilize only natural daylight. As a result, late fall and winter production of Alstroemeria cut flowers, due to reduced levels of light during these periods, typically requires 12 weeks or more of growing time from the planting of the rhizome cutting to the initiation of flowering. Even more time is required for further flowering to produce a stem ready to sale. With certain varieties, the period of time from planting to flowering can extend up to almost six months. This time will substantially vary from variety to variety, and growing techniques and conditions also affect the growing period. For example, a larger cutting will obviously require a shorter growing time than a relatively small cutting. High temperatures normally have an adverse affect on growth, as does reduced light.

The commercial implications of relatively slow growth characteristics under natural light conditions should be obvious. Increased bench or field time (if grown outdoors where climates permit) substantially increases production costs, which in turn result in increased costs per stem due to the increased cost of production. Total production of Alstroemeria cut flowers during such period is also correspondingly less. This adversely affects the normal supply/demand ratio in the marketplace, and as a result cut flowers of Alstroemeria are substantially more costly during the winter months than during the periods beginning in March when production increases. It is not unusual for stem prices to be 50% higher during the winter months of December, January, and February.

The inventor has discovered that through photoperiodic growth practices, certain cultivars can be brought into flowering in the late fall and winter periods in substantially reduced periods of time, thereby increasing production during these periods. However, all cultivars are not adaptable to photoperiodic control.

Through extensive breeding, the inventor has been able to produce new Alstroemeria cultivars, of which Liliana is one, specifically adaptable to photoperiodic control. The inventor's preferred growing technique includes growing the newly stuck plants under natural light conditions for approximately one month without light supplement. After approximately one month, the day length is effectively increased by providing four hours of artificial lighting by techniques or methods well known in the industry.

A preferred growing regimen which has provided excellent results comprises planting established rhizome divisions in ground beds near the end of August or first of September. Beginning approximately one month after planting, and continuing to April 1, the plants are subjected to light from 2:00 a.m. to 6:00 a.m. daily. A lighting system which has proved highly effective consists of 135 watt bulbs spaced every 10 feet, and hung approximately 7 feet above the ground. The bulbs are positioned in rows that are spaced 12 feet apart.

By effectively increasing the day length by means of artificial lighting, flowering can be initiated in a much shorter time. Within approximately six (6) weeks the first flower appears, and saleable stems are ready from mid-November to mid-December, depending upon the variety. In many instances, flowering is essentially continuous until June when the stems are too short to sell as cuts without heavy shading and some metod of cooling. Without shading and cooling to prolong commercial stem production, it is common practice to dig up and divide the plants. The divided plants are then stuck in late August or early September as described, and the cycle repeated. It has also been noted that the increased light regimen has resulted in longer stems, a very desirable quality.

Liliana was originated by the inventor Erwin Mojonnier from a hybridization made in a controlled breeding program in Encinitas, Calif. in 1988. The female parent was a cultivar identified as L5, a short plant with a hot pink flower, streaking on the upper and lower petals, and a yellow patch on the upper petals. The male parent of Liliana was a cultivar identified as L7, a tall plant with a pink flower, streaking on the upper and lower petals, and a yellow throat on the upper petals.

Liliana was discovered and selected as one flowering plant within the progeny of the stated parentage by Erwin Mojonnier in May 1988 in a controlled environment in Encinitas, Calif.

The first act of asexual reproduction of Liliana was accomplished when vegetative cuttings were taken from the initial selection in August 1988 in a controlled environment in Encinitas, Calif. by Erwin Mojonnier. Horticultural examination of selected units initiated in 1989 has demonstrated that the combination of characteristics as herein disclosed for Liliana are firmly fixed and retained through successive generations of asexual reproduction.

Liliana has not been observed under all possible environmental conditions. The phenotype may vary significantly with variations in environment such as temperature, light intensity and day length. The following observations, measurements and comparisons describe plants grown in Encinitas, Calif. under greenhouse conditions which approximate those generally used in commercial practice.

The following traits have been repeatedly observed and are determined to be basic characteristics of Liliana, which in combination distinguish this Alstroemeria as a new and distinct cultivar:

1. Low maintenance, with few non-flowering stems being produced.

2. Liliana is responsive to increased light for initiating flowering. By effectively increasing day length by artificial light in optimum amounts, the first flower appears approximately six weeks after rhizome planting, and saleable stems in full flower are ready by mid-November. Thus, winter production can begin relatively early and, through photoperiodic control, continue throughout the winter period. Production can therefore be effectively staggered continuously through winter periods of low natural light.

3. Liliana is easily propagated from rhizomes.

4. The background color of the flower of Liliana is a relatively bright red-purple. There is heavy streaking of grayed-purple on the upper petals, and scant marking on the lower petals. The upper petals each have a yellow patch, and there is a faint white infusion near the base of the upper petals.

5. Liliana possesses good post-harvest color retention.

The accompanying photographic drawing shows typical inflorescence and foliage characteristics of Liliana, with colors being as nearly true as possible with illustrations of this type. The photograph comprises an enlarged close-up view of an open flower of Liliana, clearly showing the parts and colors of the flower.

In the following description, color references are made to The Royal Horticultural Society Colour Chart (R.H.S.). The color values were determined between 7:00 and 7:45 a.m. on Apr. 6, 1990 under 60 foot candles of light intensity at Encinitas, Calif.

Classification: Alstroemeria cv. Liliana.
Commercial: Alstroemeria.

PLANT

Form: Cut flower.
Height: Approximately 114.3 cm. at time of harvest.
Propagation: From rhizome cuttings.
Growth Habit: Excellent.
Foliage:
- *Quantity.*—Approximately 25 leaves per stem.
- *Size of leaf.*—Approximately 14.4 cm.×2.9 cm.
- *Shape of leaf.*—Lanceolate.
- *Color.*—Upper side, green 137A; under side green 138B.

Rhizomes:
- *Color.*—White, 155B.
- *Size.*—1 cm.×1 cm. at growing tip.

INFLORESCENCE

Bud:
- *Form.*—Indeterminate.
- *Diameter.*—Approximately 1.6 cm.
- *Length.*—Approximately 4.0 cm.
- *Calyx.*—Approximately 5 mm. in diameter.
- *Peduncle.*—Length, 5.7 cm.
- *Color.*—Green, 138B.

Flower:
- *Size.*—5.6 cm. in total diameter.
- *Borne.*—5 flowers per umbel.
- *Blooming habit.*—Flowering is early, beginning in mid-November, from rhizome cuttings planted approximately September 1.
- *Shape.*—Asymmetrical.
- *Color.*—Generally, the background colors of the sepals and petals are a relatively bright red-purple. The upper petals are heavily streaked and have a yellow patch in the approximate middle third of the petal, with white being infused forward of the bases. The lower petal is lightly marked. Upper surface: Red-purple 57C. Under surface: Red-purple 61D. Other notations: There is heavy streaking on the upper two petals, fewer on the lower petal. Color on upper two petals are: Streaks: Grayed-purple 187A. Yellow patch: Yellow 2B. Lower third: White 155D.
- *Peduncle.*—Length, 11 cm.; color, green 138B.
- *Lasting quality.*—Approximately 14 days as cut flowers.

REPRODUCTIVE ORGANS

Stamens: Number, 6.
Anthers: Color, grey-brown 199C.
Filaments: Color, red-purple 62A.
Pistils: Number, 1; color, red-purple 62A.
Stigma: Color, red-purple 62A

I claim:

1. A new and distinct cultivar of Alstroemeria plant named Liliana, as illustrated and described.

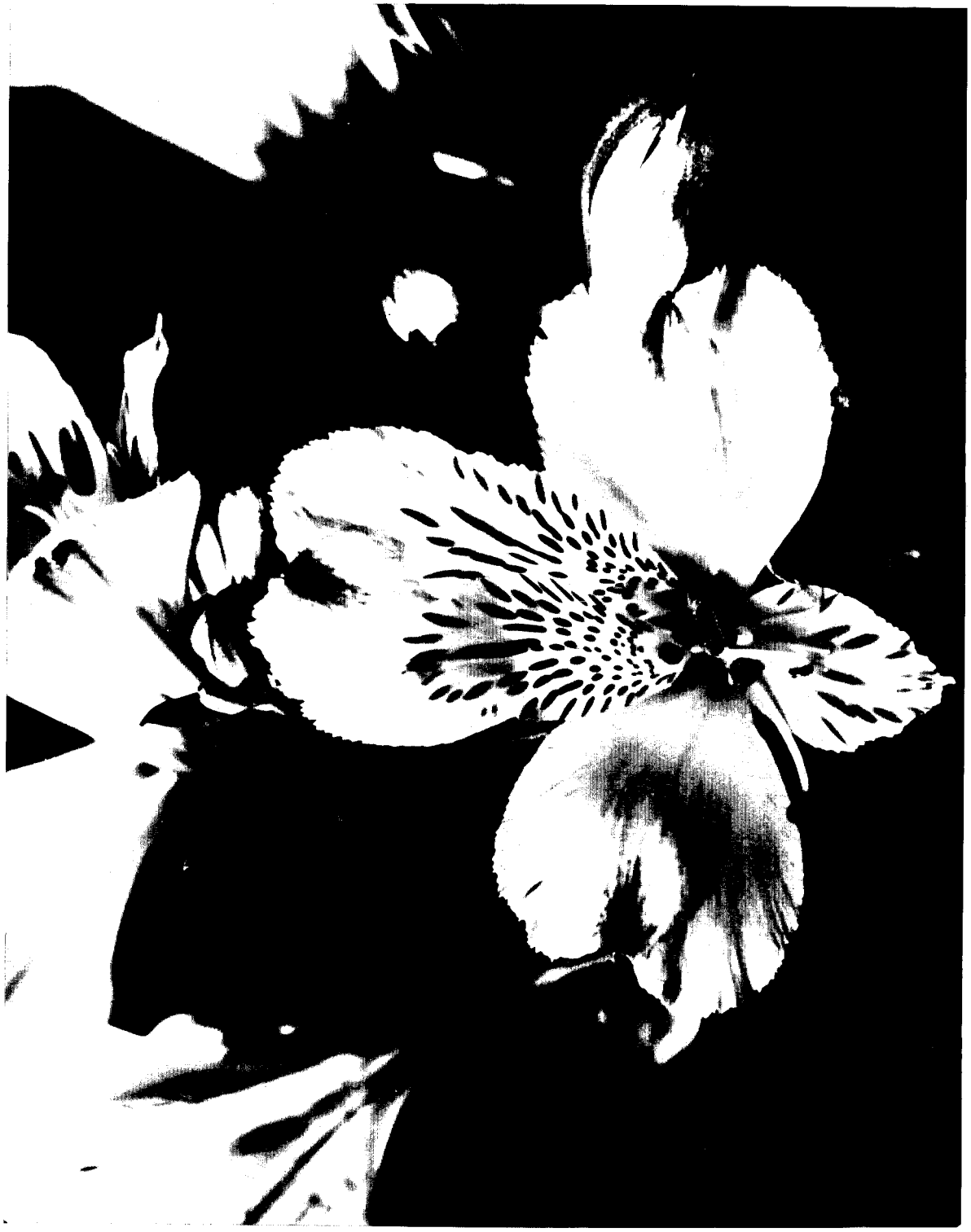

* * * * *